US008860418B2

(12) United States Patent
Badri et al.

(10) Patent No.: US 8,860,418 B2
(45) Date of Patent: Oct. 14, 2014

(54) APPARATUS AND METHOD FOR MEASURING DIELECTRIC PERMITIVITY OF CYLINDRICAL SAMPLES

(75) Inventors: Mohammed Badri, Al-Khobar (SA); Reza Taherian, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 193 days.

(21) Appl. No.: 13/560,505

(22) Filed: Jul. 27, 2012

(65) Prior Publication Data

US 2014/0028318 A1     Jan. 30, 2014

(51) Int. Cl.
| | |
|---|---|
| *G01V 3/00* | (2006.01) |
| *G01R 27/08* | (2006.01) |
| *G01R 27/04* | (2006.01) |
| *G01R 27/32* | (2006.01) |

(52) U.S. Cl.
USPC ............................ 324/376; 324/642; 324/691

(58) Field of Classification Search
CPC ... G01N 27/026; G01N 27/023; G01N 27/72; G01R 27/02; G01R 27/22; G01R 27/2647; G01R 27/2652; G01R 27/2676; G01V 3/12; H01J 37/32935
USPC ......... 324/226, 228, 262, 642, 761, 637, 645, 324/715, 727, 718, 719; 174/68.1–136, 174/75 C, 88 C
See application file for complete search history.

(56) References Cited

U.S. PATENT DOCUMENTS

| | | | |
|---|---|---|---|
| 5,077,522 A | | 12/1991 | Lahitte et al. |
| 5,157,337 A | * | 10/1992 | Neel et al. ..................... 324/632 |
| 5,389,875 A | * | 2/1995 | Rosen et al. .................. 324/228 |
| 5,541,522 A | | 7/1996 | Rosen et al. |
| 5,744,971 A | * | 4/1998 | Chan et al. .................... 324/643 |
| 6,784,854 B1 | | 8/2004 | Yukl |
| 7,560,937 B2 | * | 7/2009 | Bini et al. ...................... 324/634 |
| 8,183,878 B2 | * | 5/2012 | Sekino ..................... 324/754.15 |
| 8,403,679 B2 | * | 3/2013 | Berard et al. ................... 439/24 |
| 2005/0146348 A1 | | 7/2005 | Howland et al. |
| 2010/0156439 A1 | | 6/2010 | Schroeder et al. |

OTHER PUBLICATIONS

Nyshadham, et al., "Permittivity measurements using open-ended sensors and reference liquid calibration-an uncertainty analysis", IEEE Transactions on Microwave Theory and Techniques, vol. 40(2), 1992, pp. 305-314.

International Search Report and Written Opinion issued in PCT/US2013/051010 on Oct. 18, 2013, 17 pages.

* cited by examiner

*Primary Examiner* — Huy Q Phan
*Assistant Examiner* — Raul Rios Russo
(74) *Attorney, Agent, or Firm* — Bridget Laffey; Jakub M. Michna

(57) ABSTRACT

An open ended coaxial probe is disclosed that can be used to measure the dielectric properties of solids. According to some embodiments, the probe is specially designed to make good contact with solids having flat or non-flat surfaces. This design relies on forcing a good contact between the solid surface with both the center conductor and outer conductor of the coaxial probe. A method is also described in which the coaxial probe is used to monitor the dielectric permittivity of cylindrical samples such as rock cores drilled from a well. Also described are methods of using the coaxial probe to provide a continuous log of the dielectric permittivity of a rock core.

29 Claims, 10 Drawing Sheets

APPARATUS AND METHOD FOR MEASURING DIELECTRIC PERMITIVITY OF CYLINDRICAL SAMPLES

BACKGROUND

Open-ended coaxial sensors are routinely used in measuring the dielectric permittivity of materials using the reflection of high frequency radiation from the interface between the open end and the material under investigation. This probe measures the scattering parameter (S11) and uses it to derive the reflection coefficient from the interface. The reflection coefficient is related to impedance difference between the two media in the interface and is given by: $\gamma=(Z1-Z2)/(Z1+Z2)$, where Z1 and Z2 refer to the impedances of the medium under investigation and the coaxial probe. Knowing the impedance of the open ended coax and the reflection coefficient allows calculating the impedance and thus the dielectric permittivity of the medium under investigation.

A problem with using a conventional open-ended coaxial probe is its shallow depth of investigation. As a result the sensor is quite good and easy to use for measuring the dielectric properties of liquids where there is a good contact between the end of the probe and the liquid. Using the probe to measure the dielectric properties of solids is more challenging since a small gap between the probe and the solid can lead to large errors. Currently there exists a commercial open-ended coaxial sensor for dielectric measurement of liquids. The application of any open ended coaxial probe to measure solid samples is limited to flat surfaces at best.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a coaxial-based sensor probe for making dielectric measurements of a solid sample is described. The probe includes: a central conductor having a tip for contacting a surface of the solid sample, the central conductor defining a longitudinal axis of the probe; a dielectric material surrounding at least a portion of the central conductor; an outer conductor surrounding at least a portion of the dielectric material, and having a circular cross section in a plane perpendicular to the longitudinal axis along at least a portion of the outer conductor; and a shaped conductor having a circular cross section in a plane perpendicular to the longitudinal axis along a portion of the shaped conductor and having an edge shape that corresponds to an expected shape of a non-flat surface of the solid sample, wherein the outer conductor and shaped conductor are arranged such that the outer and shaped conductors are centered about the longitudinal axis and are in electrical contact with each other. The dielectric material may be air, or a solid material such as ceramic, glass or plastic. According to some embodiments, the shaped conductor and outer conductor are dimensioned such that the shaped conductor slides along an outer surface of the outer conductor while maintaining electrical contact with the outer conductor. In such cases, one or more springs can be used to apply a spring force between the outer conductor and the shaped conductor in directions parallel to the longitudinal axis.

According to some embodiments the edge shape of the shaped conductor corresponds to a convex (such as cylindrical) or concave shaped surface of the sample material. According to some embodiments, the shaped conductor is removable from the sensor probe and is replaceable with one or more differently shaped conductors.

According to some embodiments, the solid material is a core sample of rock from a subterranean rock formation.

According to some embodiments a sensor probe system is also described that includes the sensor probe as described, as well as electronics configured to apply high frequency radiation into a solid sample from the central and shaped conductors. The electronics may be configured to measure a scattering parameter, and to derive therefrom a reflection coefficient from an interface between the sensor probe and the sample material. According to some embodiments dielectric permittivity is derived based on the scattering parameter measurements. The sensor probe system can also include a stepper motor system positioned and configured to move the sensor probe into contact with the solid material at a plurality of location on the solid material. According to some embodiments the electronics is also configured to derive an anisotropy parameter of the solid sample, such as based on multiple measurements at orthogonal directions of the sample material.

According to some embodiments a method is described of making dielectric measurements from a non-flat surface of a solid material using a coaxial sensor probe. The method includes moving a central conductor and a shaped conductor of a coaxial-based sensor probe into contact with the non-flat surface of the solid material, the shaped conductor having a circular cross section in a plane perpendicular to a longitudinal axis of the central conductor, and the shaped conductor having an edge shape that corresponds to the non-flat surface of the solid sample.

According to some embodiments, the method also includes a step-wise mode including making a first measurement with the sensor probe in contact with the solid material at a first location; retracting the sensor probe away from the first location of the solid material using the motor system; moving the sensor probe relative to the solid material and moving the sensor probe into contact with the solid material at a second location; and making a second measurement with the sensor probe in contact with the solid material a the second location.

According to some other embodiments, the method includes a scratch-mode of operation that includes moving the sensor probe relative to the solid material while maintaining contact with the solid material; and making a series of measurements with the sensor probe as it is moved relative to the solid material.

According to some other embodiments, the method includes pushing the central conductor through the non-flat surface of the sample material so as to create an indentation on the non-flat surface, and deriving one or more mechanical properties of the sample material based at least in part on the pushing of the central conductor through the non-flat surface of the sample material.

According to some embodiments, a coaxial-based sensor probe for making dielectric measurements of a solid sample is described. The probe includes: a central conductor having a tip for contacting a surface of the solid sample, the central conductor defining a longitudinal axis of the probe; a dielectric material surrounding at least a portion of the central conductor; and an outer conductor surrounding at least a portion of the dielectric material, and having a circular cross section in a plane perpendicular to the longitudinal axis along at least a portion of the conductor, the outer conductor including an edge shape and position relative to the central conductor tip that corresponds to an expected shape of a non-flat surface of the solid sample such that electrical contact between the central conductor tip and the non-flat surface and electrical contact between the outer conductor and the non-flat surface are suitable for dielectric measurements of the solid sample. According to some embodiments, the outer conductor can have an edge shape corresponding to a convex or concave cylindrical sample shape. According to some other embodiments the outer conductor edge extends beyond the central conductor tip (or visa versa) which corresponds to a convex (or concave) spherical non-flat surface.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details of the subject disclosure in more detail than is necessary for the fundamental understanding of the subject disclosure, the description taken with the drawings making apparent to those skilled in the art how the several forms of the subject disclosure may be embodied in practice. Further, like reference numbers and designations in the various drawings indicate like elements.

According to some embodiments, an open ended coaxial probe is disclosed that can be used to measure the dielectric properties of solids. According to some embodiments, the probe is specially designed to make good contact with solids having flat or non-flat surfaces. This design relies on forcing a good contact between the solid surface with both the center conductor and outer conductor of the coaxial probe. A method is also described in which the coaxial probe is used to monitor the dielectric permittivity of cylindrical samples such as rock cores drilled from a well. Also described are methods of using the coaxial probe to provide a continuous log of the dielectric permittivity of a rock core.

According to some embodiments a coaxial-based probe sensor is described which significantly reduces or in some cases eliminates any gap between the open ended coaxial probe and the medium under investigation.

Figure 1:
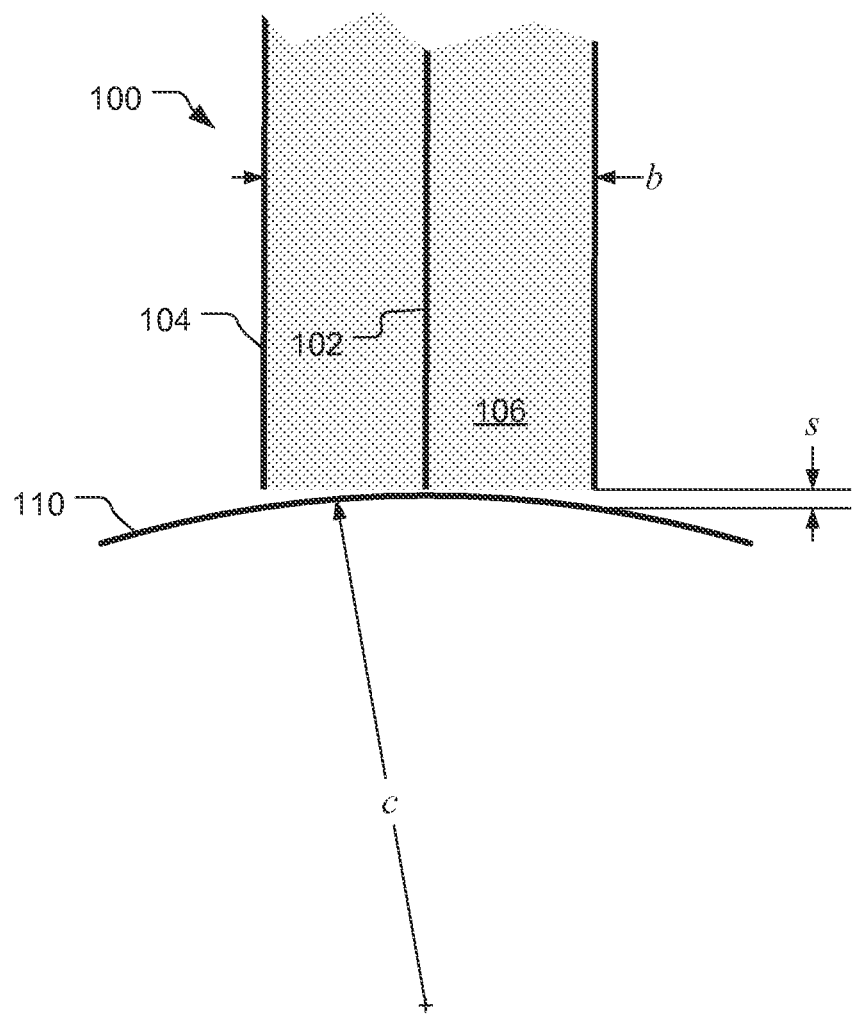
FIG. 1 is a diagram illustrating a gap between a conventional open ended coaxial probe and a non flat material sample.

FIG. 1 is a diagram illustrating a gap between a conventional open ended coaxial probe and a non flat material sample. The coaxial probe 100 includes an inner conductor 102 and an outer conductor 104, as well as a dielectric insulating material 106. Note that in the case of FIG. 1, there is a gap between the sample 110 and the outer conductor 104. The sample 110 (such as a rock core) has a diameter c touched by an open ended coaxial probe 100 of diameter b. For simplicity in this example, we assume the rock surface of sample 110 is smooth but curved, while the open end of the coax probe 100 is flat, which leads to a gap between the two surfaces.

As a result of curvature in the shape of the core sample, there is a need for a proportional extra length, s, between the outer conductor 104 and inner conductor 102 of the coaxial probe 100 to ensure both inner and outer conductors are touching the sample. This difference can be calculated based on the geometry of the core and the diameter b of the coaxial probe 100 (for simplicity, we ignore the wall thickness of the coax outer conductor). In this example, there would be a gap between the outer conductor 104 of the coax and the surface of the rock 110.

Figure 2:
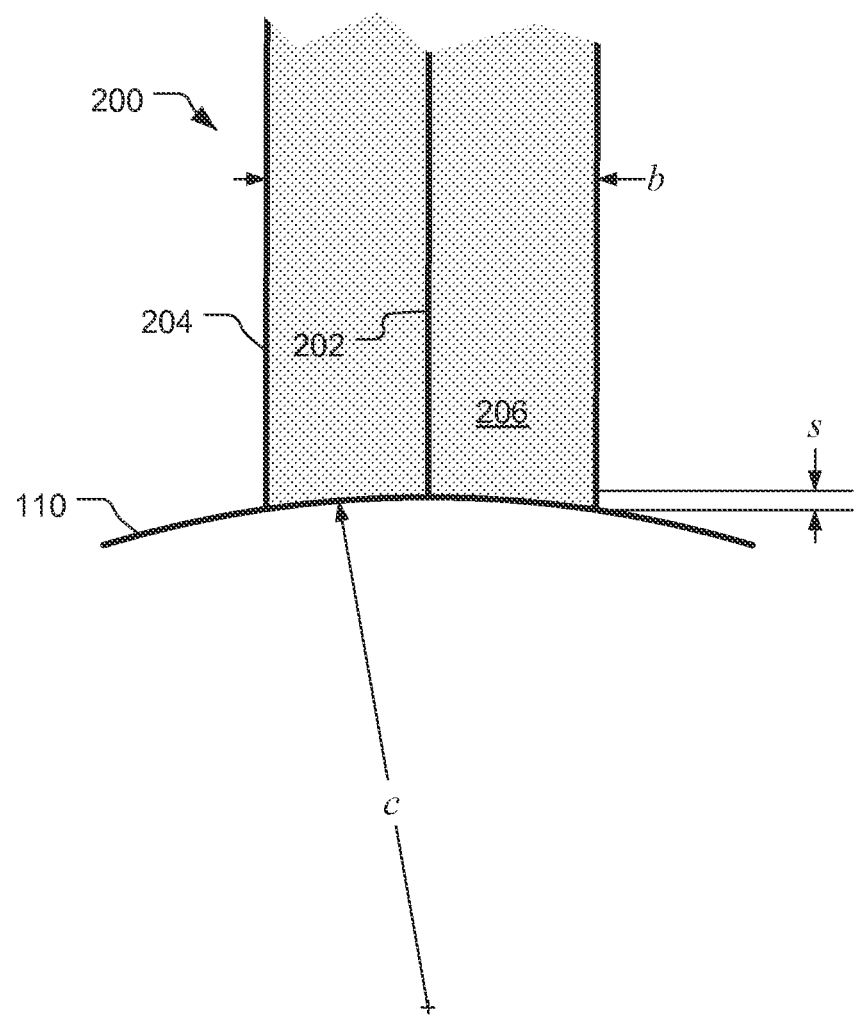
FIG. 2 is a cross section view of a coaxial probe for making measurements on curved surfaces, according to some embodiments.

FIG. 2 is a cross section view of a coaxial probe for making measurements on curved surfaces, according to some embodiments. The coaxial probe 200 has central conductor 202, outer conductor 204 and a dielectric material 206. The dielectric material 206 may be air, or a solid material such as ceramic, glass or plastic. The probe 200 has had a shape correction to match the curvature c of the sample 110. The shape can be altered, for example by machining the appropriate curvature in the outer conductor 204 if the c is known. The resulting geometry is shown in the cross-sectional view of FIG. 2. The probe 200 is particularly suitable when c is constant at the point of contact.

However, for many samples, such as the cores cut from oil wells, the curvature radius c varies from one well to the next. For such cases, a probe designed for a fixed value of c such as probe 200 shown in FIG. 2 will not be suitable. Variation in the diameter of the core along its length, also leads to a variation in local curvature which affects the potential gap distance s. In such cases, the potential gap s can vary from one core sample to the other and it can also vary along the length of the same core sample.

Figure 3A:
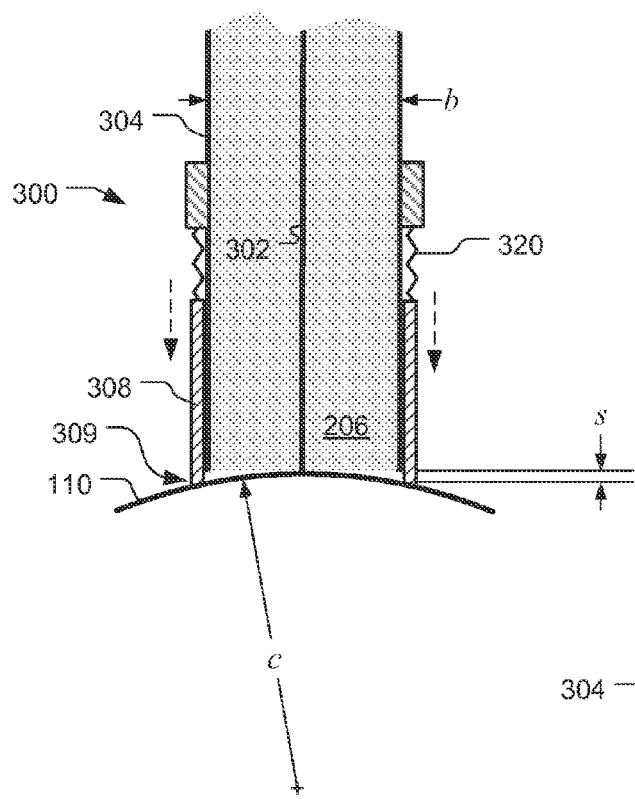
FIGS. 3A-3B are a cross section and a prospective view, respectively, of coaxial probe for use when the sample material has a convex geometry, according to some embodiments.
Figure 3B:
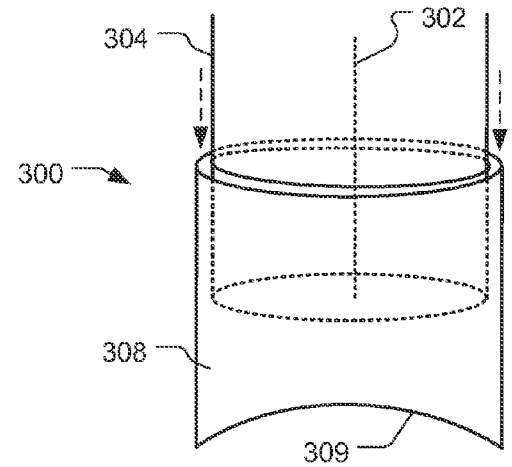

FIGS. 3A-3B are a cross section and a prospective view, respectively, of coaxial probe for use when the sample material has a convex geometry, according to some embodiments. With probe 300, the length of outer conductor is adjusted in real time by providing a sleeve 308 that surrounds the outer conductor 304 and can be pressed against the core sample 110. As long as the curvature of the (core) sample 110 does not completely reverse itself, the outer conductor has to be longer than the inner conductor by s and s is to be adjustable on the fly in realtime. According to some embodiments, the shape of the transition 309, which is the lower edge of the sleeve 308 is contoured to match the sample 110 having a radius of c. In the example shown in FIGS. 3A-3B, the pressing of the sleeve can be done by a spring 320 which applies force to the sleeve 308 in the direction indicated by the dashed-line arrows. The spring force from spring (or springs) 320 is such that the sleeve 308 makes good contact with the sample.

The inner diameter of the movable sleeve 308 is made slightly greater but very close to the outer diameter b of the outer conductor 304 enabling the movable cylinder to be in good electrical contact with the outer conductor 304 of the coax and together, the conductor 304 and sleeve 308 provide a continuous path for the flow of electric current. Note that the distance between the end of coaxial outer conductor 304 and the end of movable sleeve 308 is relatively short and in particular on the order of magnitude or smaller than the coax diameter, b.

In some industrial applications, such as a factory that makes pipe or rod shaped products, the diameter c is very well controlled and a single sleeve having a specifically designed transition shape will suffice. However in cases where the potential samples have various shapes then, according to some embodiments, different sleeves with other transition shapes can be used.

Figure 3C:
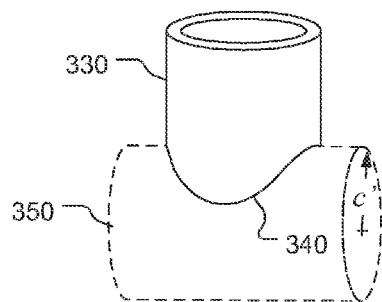
FIGS. 3C-3E illustrate various shapes of transition sleeves for use with different shapes of samples, according to some embodiments.
Figure 3D:
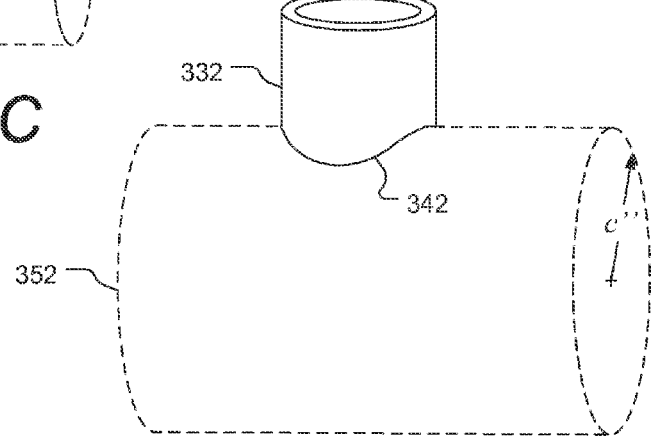
Figure 3E:
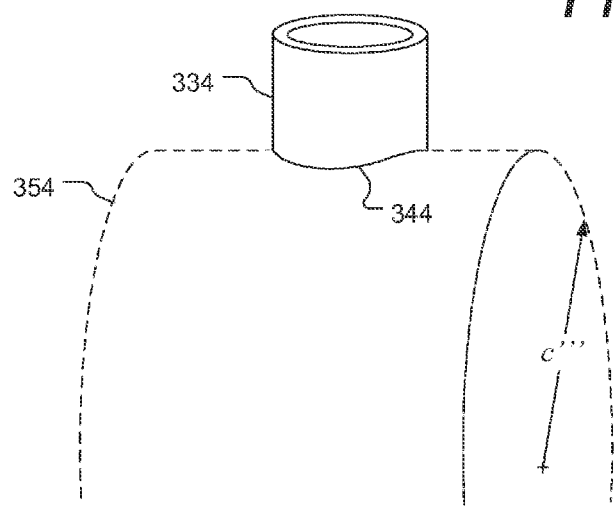

FIGS. 3C-3E illustrate various shapes of transition sleeves for use with different shapes of samples, according to some embodiments. FIG. 3C shows a moveable sleeve 330 that has a shaped transition 340 adapted to a sample 350 having a radius of c'. Similarly, FIGS. 3D and 3E show moveable sleeves 332 and 334 that has a shaped transitions 342 and 344 respectively, that are adapted to sample 352 and 354 having a radii of c'' and c''', respectively. According to some embodiments, the variously shaped sleeves 330, 332 and 334 are adapted to replace sleeve 308 in the probe 300 shown in FIGS. 3A and 3B. It has been found that for relatively small variations in the sample radius c the transition shape does not need to be changed. However, for larger variations in the sample radius c it is beneficial to change the sleeve to one that is more closely matched to the particular sample shape. According to some embodiments a "kit" is provided in which a single probe body (including the spring(s) 320, outer conductor 304, the dielectric 206 and central conductor 302) can be mated to any one of several included sleeves each having transition shapes for a different shape of sample. The number of sleeves in some cases is 5, but can be any number such as 3 or 10 sleeves. Such a kit has the advantage of being very practical as well as providing high accuracy measurements due to minimizing the gap size between the probe and the sample.

According to some embodiments, in cases where the sample (such as rock core) diameter varies too much along the length of the sample, the sample is mechanically trimmed to be within certain acceptable range of diameters. However, since this method modifies the core, in some cases this may not be suitable.

According to some other embodiments, in cases where the sample (such as rock core) diameter varies too much along the length of the sample, the scan is repeated using a few different sleeves (having different transition shapes). The data from the multiple scans is treated when combined. Treating may comprise, for example, using the known local core diameter and picking and choosing the data from the most appropriate transition for that section based on the known core diameter.

In cases where the samples are relatively rough, such as rock cores from the oil wells, the center conductor will make good contact, but the transition may not. Thus in order to minimize error, it is desirable to maximize the contact between the core and the transition. This is in contrast to measuring a core with a conventional, flat end, probe where the outer conductor contacts the ridge of the core.

Thus, in addition to the mechanical advantages, many of the embodiments described herein have electrical measurement benefits. By using a shaped outer conductor as described herein the outer conductor either substantially contacts the core or at least comes much closer to the sample than when using a conventional flat probe. The close proximity reduces measurement error since high frequency energy can travel through small gaps. Of course some error will still be introduced with any gap, since this part is not accounted for, but the error is much less than when using a conventional flat end probe.

Figure 4A:
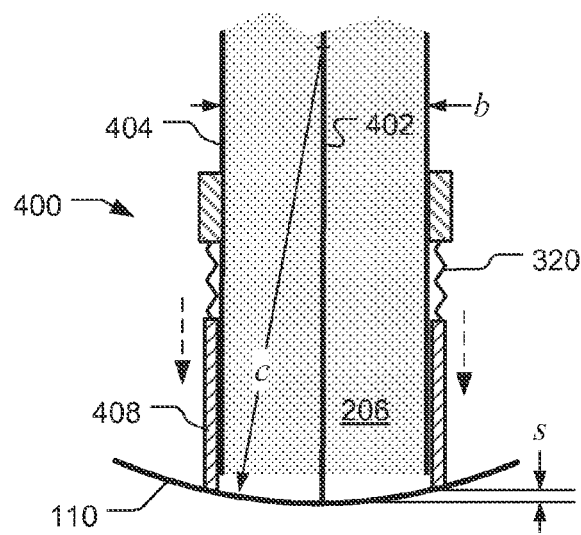
FIGS. 4A and 4B are a cross section and a prospective view, respectively, of coaxial probe for use in cases when the sample has concave geometry, according to some embodiments.
Figure 4B:
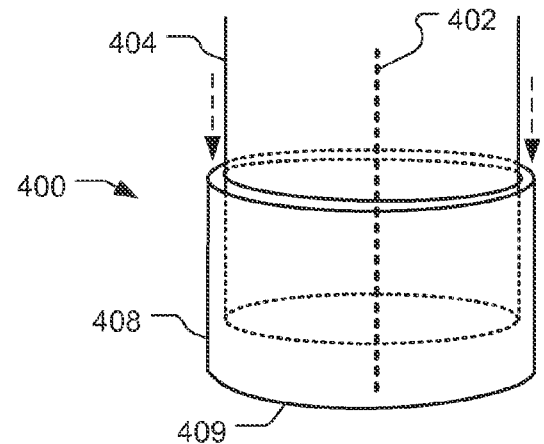

FIGS. 4A and 4B are a cross section and a prospective view, respectively, of coaxial probe for use in cases when the sample has concave geometry, according to some embodiments. If a conventional flat coax probe is used, a gap s is formed between the sample 110 and the inner conductor of the coax probe. According to some embodiments, a spring loaded sliding outer sleeve is used in coaxial probe 400 in a similar fashion as with probe 300 shown in FIGS. 3A and 3B. As is shown in FIGS. 4A and 4B, the probe 400 works for concave samples, such as sample 110, provided the inner conductor 402 of the coax is longer than the outer conductor 404 by at least s and the front edges of the movable sleeve 408 are machined to accommodate the concave shape. In the case shown in FIG. 4A, the sample 110 has a simple cylindrical trough shape. As in the case of probe 300, in probe 400 springs 320 apply force to the sleeve 408 in the direction shown by the dashed-line arrows. According to some embodiments, the shape of transition 409 of sleeve 408 is similar or identical to that of sleeves 308, 330, 332 or 334. In such cases the sleeve orientation is rotated about the probe's central axis by 90 degrees to accommodate a concave cylindrically shaped sample instead of a convex cylindrically shaped sample.

Figure 5:
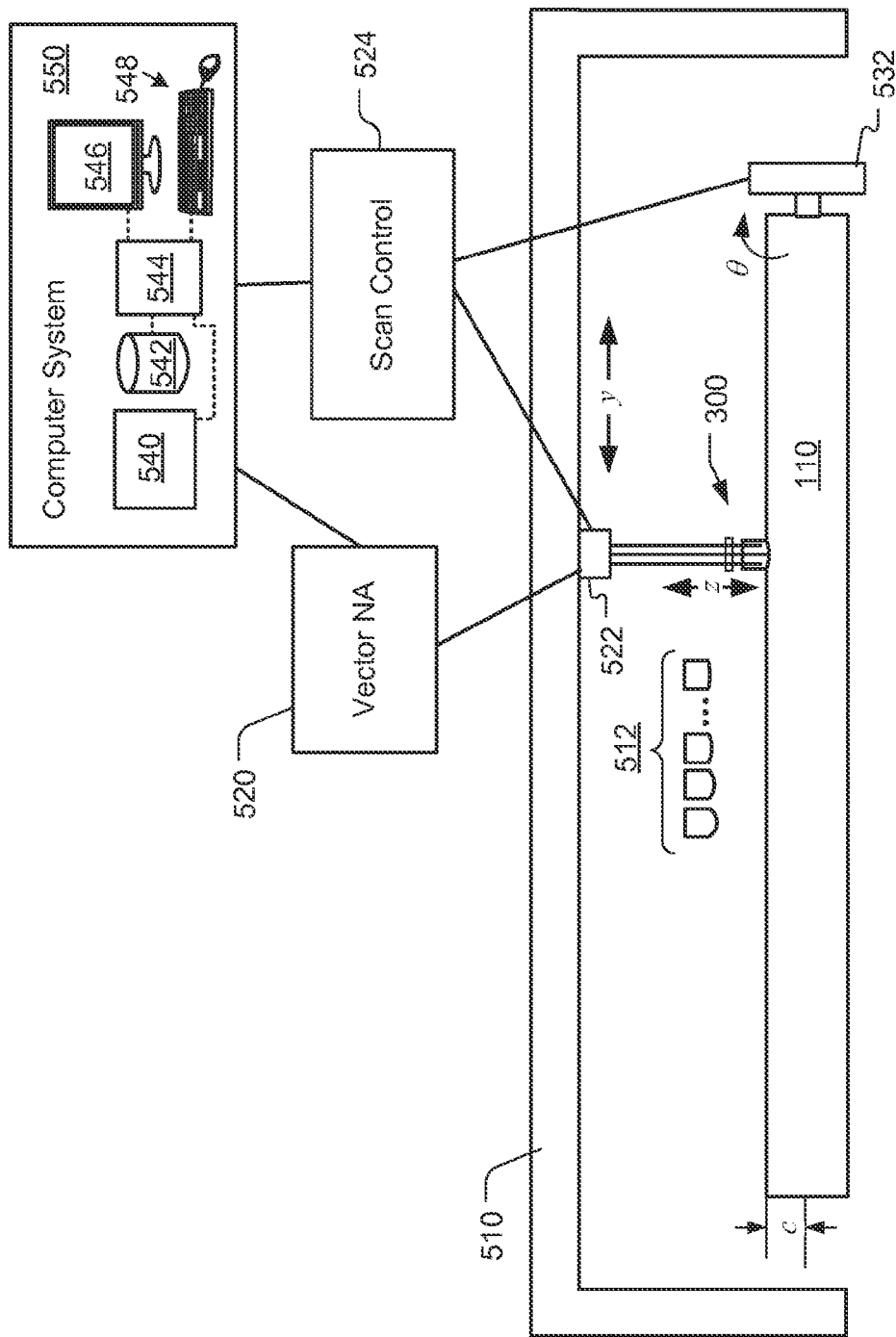
FIG. 5 is a diagram illustrating a system for making measurements of a non-flat solid sample using a coaxial probe, according to some embodiments.

FIG. 5 is a diagram illustrating a system for making measurements of a non-flat solid sample using a coaxial probe, according to some embodiments. In the set up shown, the probe 300 is mounted to a stepper motor 522 which is in turn mounted to a frame 510. The stepper motor 522 can move the probe 300 towards and away from the sample 110 (shown as the z direction), as well as along the length of the sample 110 (shown as the y direction). According to some embodiments, a sleeve selected from a number of sleeves 512 having different transition shapes can be mounted to the probe body of probe 300. For example, the set of sleeves 512 can include various sleeves having shaped transitions for different convex shaped samples (such as sleeves 308, 330, 332 and 334 shown in FIGS. 3A-3E). According to some embodiments the set can also include one or more sleeves having a transition shaped for concave samples, such as sleeve 408 shown in FIGS. 4A and 4B, and/or transitions shaped for spherical samples such as sleeve 708 shown in FIG. 7. The set up also includes a scan control unit 524 for controlling the sequence of positions of the probe and a vector network analyzer 520 for making electrical (S11) measurements. The scan control unit 524 and the network analyzer 520 are both under the control of a computer system 550. The computer system 550, according to some embodiments, includes a storage system 542, communications and input/output modules 540, a user display 546 and a user input system 548.

According to some embodiments, various modes of operation will now be described in further detail with reference to the set up shown in FIG. 5. The dielectric probe 300, or another probe such as probes 200, 400, 700, 800 and/or 900, can be utilized in step mode wherein a measurement is performed at one position and then the probe is lifted and moved to a second location for making the next measurement. For each measurement, care is taken to ensure good contact between the sample and the coax center conductor as well as the movable sleeve. Each one of these objectives is achieved by providing a mechanism (such as a spring in the case of probes 300, 400 and 700) for application of the probe to the sample. According to some embodiments, a stepper motor system including stepper motor 522 and scan control unit 524 is used to lift and move the probe, and a network analyzer 520 or similar instrument is used to perform the reflection (S11) measurements. Computer system 550 is used to collect and process the data. With this mode of operation there is very good contact between the probe end and the surface of the sample. Also, with this mode of operation the probe does not need to be designed to a particularly rugged specification. Further, the distance between measurement points can be selected by the user and are limited by the resolution of the stepper motor.

According to some embodiments, a second mode of operation is provided in which the probe is brought down to touch the sample surface and then dragged along the rock while making measurement. In this mode, sometimes referred to as a scratch mode, stepper motor 522 is used to force the coax center conductor for good contact with the rock surface, and such force plays a role on the accuracy of the data. Note that the force application system (such as stepper motor 522) is in addition to the mechanism used to force the movable sleeve (such as spring(2) 320 in FIG. 3A). As the coaxial probe scratches the surface of the sample, it will generate a corresponding heat, which will increase the temperature of the probe and needs to be accommodated in the probe's design. According to some embodiments, the probe temperature is controlled by flow of air or inert gas in the probe to cool the probe down. In addition, when operating in a scratch mode the coaxial probe is ruggedized to resist excessive wear. According to some embodiments, a metal alloy such as Inconel is used, or another that is both conductive and has the appropriate mechanical properties for making ruggedized coaxial probe.

The scratch mode of operation can potentially provide more data than the step-wise mode. The number of data points is related to the sampling rate, which is the time the network analyzer takes to make and record one measurement and start the second, or how fast the probe is moved along the core length. Using a scratch mode it is possible to map higher resolution measurements in shorter times since the probe does not have to be lifted up and brought down on the next location.

According to yet other embodiments, a mode of operation is provided wherein the inner conductor is forced into the sample creating a small indentation into the sample. The indenting mode provides the best contact between the center conductor and the sample and leads to very accurate results but in this case the center conductor should be made even more rugged than when using step-wise or scratch modes. According to some embodiments, known techniques for using a needle like probe to make an indentation in a rock sample are used in the design of the central conductor. For example, see the TSI instrument made by TerraTek, which is dedicated to scratch testing rock samples. The indentation is used to measure the mechanical properties of the sample (such as a rock), which may be used for other purposes. In this mode when the center conductor of the coax is pressed into the sample, the required force and the depth of indentation is measured which provides information on the mechanical properties of the sample. The mechanical properties include uniaxial compressive stress (UCS) of the sample. At the same time the movable sleeve makes contact with the surface of the sample while the probe is making reflection measurement leading to dielectric permittivity of the rock. In this mode, the permittivity and mechanical properties are measured in situ and the data can be used to relate these properties.

According to some embodiments, anisotropy analyses are made using techniques described herein. Rocks are known to be anisotropic, meaning that their properties (resistivity, dielectric, sonic, etc.) measured in one direction are not necessarily the same when measured in another direction.

The anisotropy is either intrinsic wherein the material by its nature is anisotropic or it can be caused by the rock layer having streaks of other material embedded in its structure. The latter is very common in hydrocarbon-bearing reservoir rocks. In the deposition period of the material that later turns into a rock, there may be many different geological events that introduce other materials into the deposition sequence. Once the deposition is buried and turned into a rock the added material would act as a source of geometrical anisotropy.

In particular, it is not unusual for the rocks to be laminated wherein a sequence of sandstone and shale layers form a structure. When dealing with such samples, interplay between the sensor's resolution, the thickness of the beddings, and the relative orientation of the bedding to the sensor can lead to anisotropic measurements. For example, if the sensor resolution is large enough to sample more than one layer at a time and the direction of beddings is not perpendicular to the scanning axis of the sensor the measurements will be anisotropic.

Figure 6A:
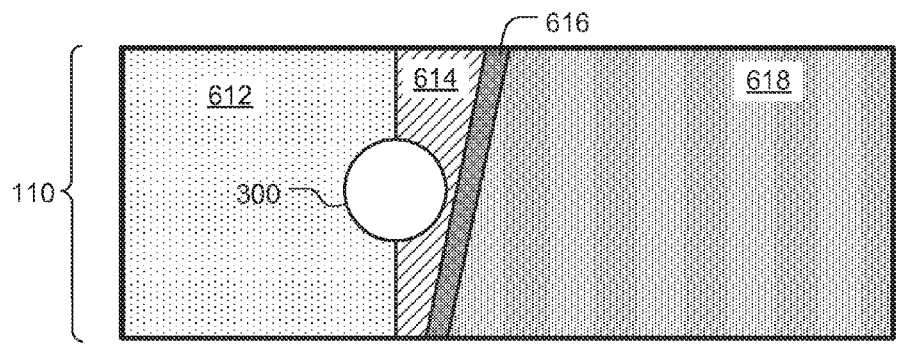
FIGS. 6A and 6B are diagrams illustrating measurements being made on a core sample in two orthogonal orientations, according to some embodiments.
Figure 6B:
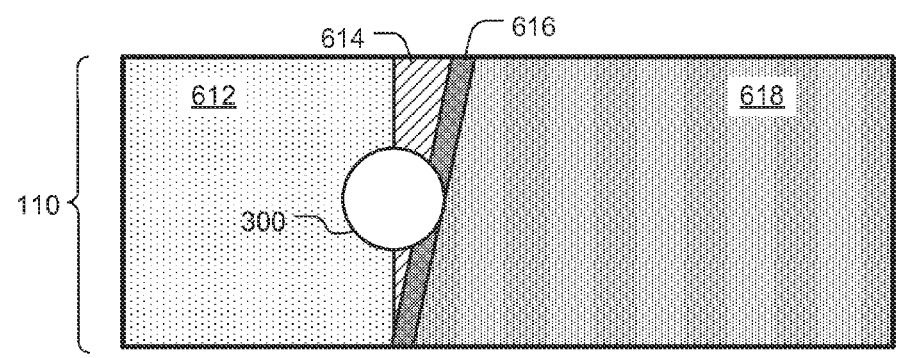

FIGS. 6A and 6B are diagrams illustrating measurements being made on a core sample in two orthogonal orientations, according to some embodiments. In each case, the top view is shown for clarity. The core sample 110 has four layers shown as 612, 614, 616 and 618. The spot size of the measurement sensor 300 is shown as a circle. In the orientation shown in FIG. 6A, the sensor 300 will measure a combination of properties from layers 612 and 614 while in the orientation shown in FIG. 6B, the same sensor 300 at the same location (in the y direction as shown in FIG. 5) will measure contributions from layers 612, 614, and 616. This difference in measurement values is an indication of anisotropy. From the example shown in FIGS. 6A and 6B, it can be seen that if the sensor 300 is in a location where it's spot size is located on one of the layers, any difference in measurements in the two perpendicular orientations (if any) is due to intrinsic anisotropy. However, at the location of the spot size schematically depicted in FIGS. 6A and 6B, the anisotropy is due to a combination of the intrinsic and geometrical. Usually, the geometrical anisotropy is more prominent in rocks.

Referring again to FIG. 5, the setup shown can be used to record the dielectric (permittivity as well as conductivity) anisotropy of the sample by making a measurement in one orientation and then rotating the sample and repeating the measurement. The sample can be mounted on a holder that includes a rotational motor 532 under control of the scan control unit 524 to change the orientation angle θ. According to some other embodiments, two or more orthogonally arranged sensors 300 can be mounted to the frame so as to scan the sample 110 at orthogonal directions at the same time.

The procedure for converting the phase and amplitude of S11 as measured by the probe to dielectric permittivity and conductivity is well known in the art. See the reference (Nyshadham et al., IEEE Transactions on Microwave Theory and Technique, 1992, Vol. 40(2), P 305) as an example, which is incorporated by reference herein.

Figure 7:
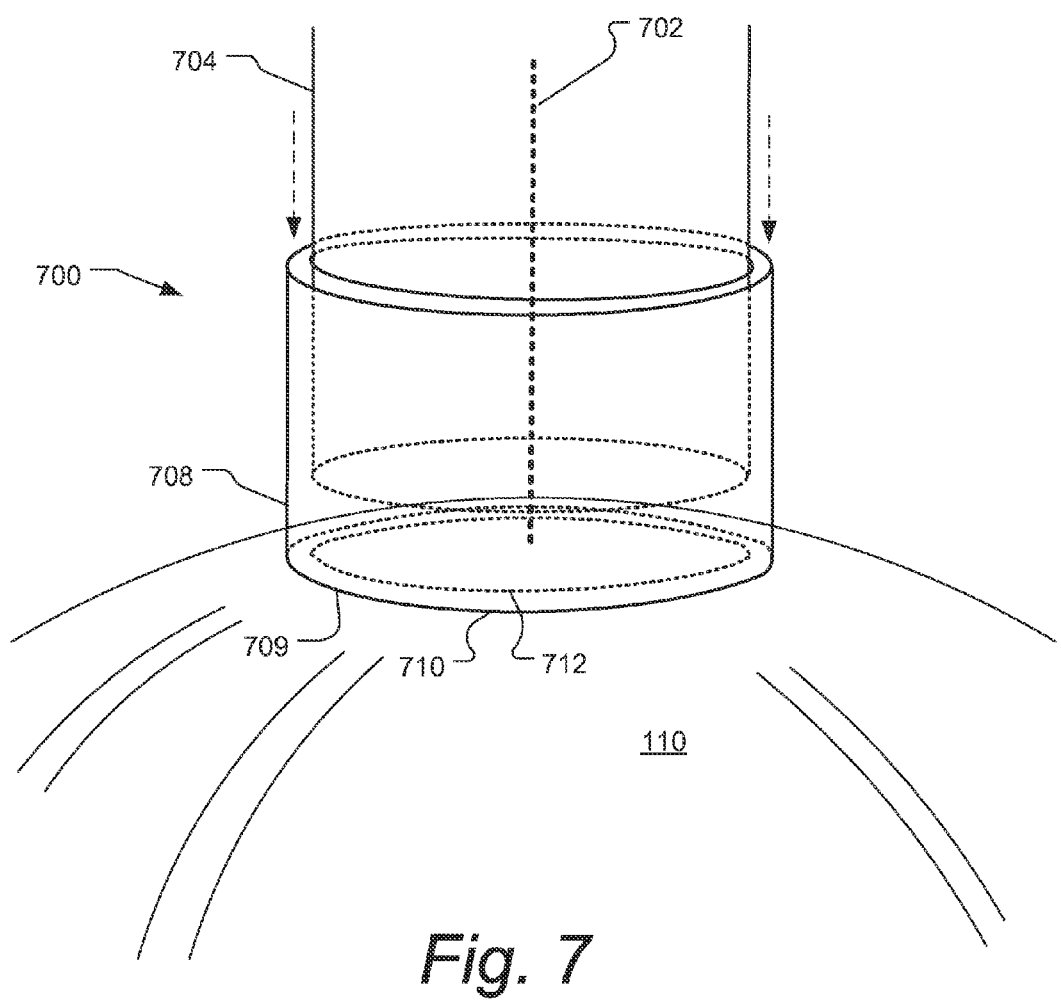
FIG. 7 is a prospective view of a coaxial probe for use when the sample material has a spherical convex geometry, according to some embodiments.
Figure 9:
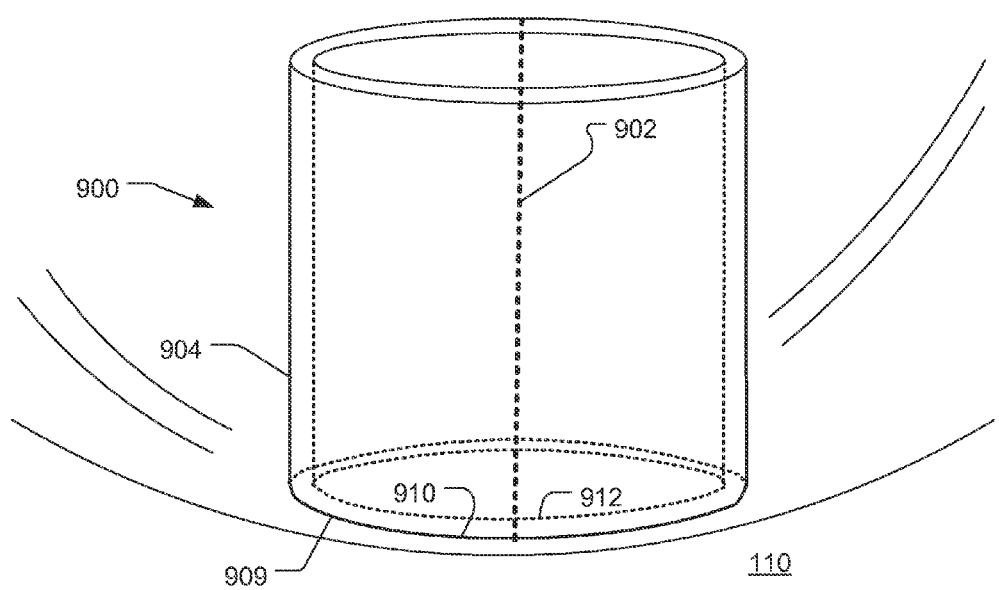
FIG. 9 is a prospective view of a coaxial probe for use when the sample material has a spherical concave geometry, according to some embodiments.

FIG. 7 is a prospective view of a coaxial probe for use when the sample material has a spherical convex geometry, according to some embodiments. As with probes 300 and 400 described above, the probe 700 includes a sleeve 708 that slides with respect to, while maintaining electrical contact with, the outer conductor 704. The sleeve 708 can be pressed against the sample material 110 with the aid of one or more springs (not shown). The sleeve 708 has transition 709 that includes an outer rim 710 and an inner rim 712. According to some embodiments, where the expected shape of the solid sample 110 is convex spherical, as shown in FIG. 7, the outer rim 710 extends slightly more than the inner rim 712. According to other embodiments, where the expected shape of the solid sample is concave spherical (such as shown in FIG. 9), the outer rim 710 extends slightly less than the inner rim 712. According to yet other embodiments, the transition 709 is flat, but the spring-loaded sliding action of the sleeve 708 ensures good electrical contact of the solid surface with both the sleeve transition 709 and the central conductor 702.

Figure 8:
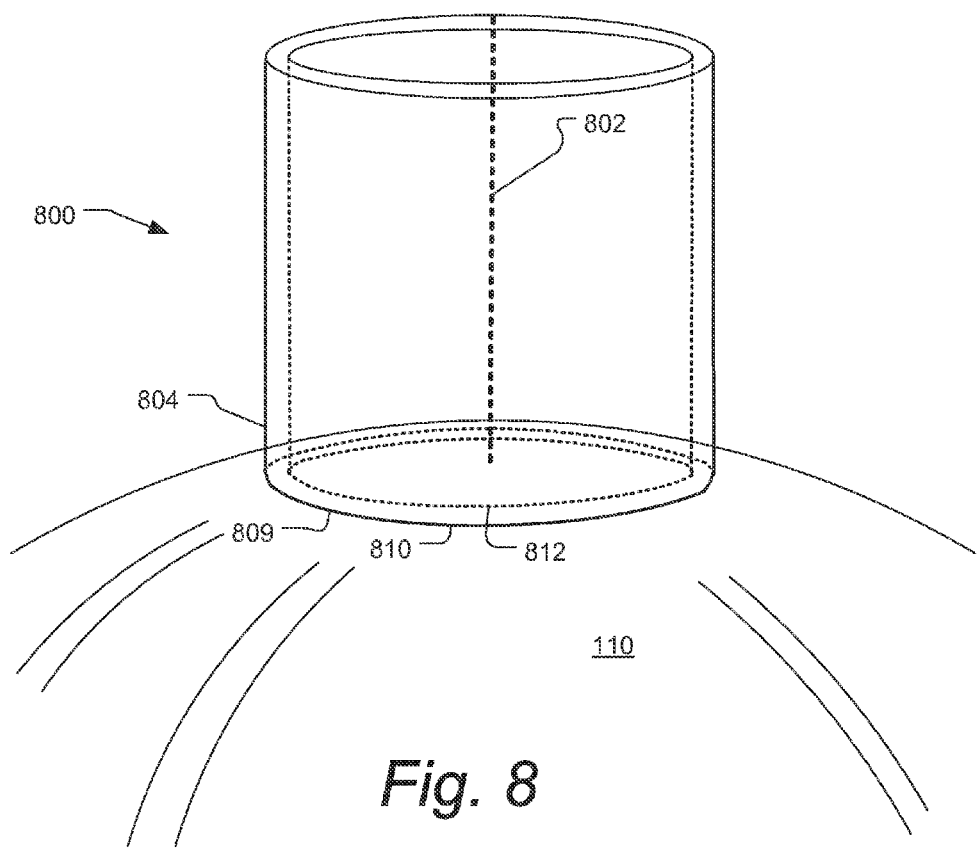
FIG. 8 is a prospective view of a coaxial probe for use when the sample material has a spherical convex geometry, according to some embodiments.

FIG. 8 is a prospective view of a coaxial probe for use when the sample material has a spherical convex geometry, according to some embodiments. The probe 800 includes a central conductor 802, an outer conductor 804 and a dielectric material in between (not shown). The probe 800 is adapted for contact with a spherical convex solid sample by making the transition 809 of the outer conductor 804 extend pass the level of the inner conductor 802. According to some embodiments, the outer rim 810 of conductor 804 extends slightly more than the inner rim 812, and according to other embodiments the end of conductor 804 is flat.

FIG. 9 is a prospective view of a coaxial probe for use when the sample material has a spherical concave geometry, according to some embodiments. The probe 900 includes a central conductor 902, an outer conductor 904 and a dielectric material in between (not shown). The probe 900 is adapted for contact with a spherical convex solid sample by making the inner conductor 902 extend pass the level of the transition 909 of the outer conductor 904. According to some embodiments, the outer rim 910 of conductor 904 extends slightly less than the inner rim 912, and according to other embodiments the end of conductor 904 is flat.

While the subject disclosure is described through the above embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the subject disclosure should not be viewed as limited except by the scope and spirit of the appended claims.

What is claimed is:

1. A coaxial-based sensor probe for making dielectric measurements of a solid sample, the probe comprising:
    a central conductor having a tip for contacting a surface of the solid sample, the central conductor defining a longitudinal axis of the probe;
    a dielectric material surrounding at least a portion of the central conductor;
    an outer conductor surrounding at least a portion of the dielectric material, and having a circular cross section in a plane perpendicular to the longitudinal axis along at least a portion of the outer conductor;
    a shaped conductor having a circular cross section in a plane perpendicular to the longitudinal axis along a portion of the shaped conductor and having an edge shape that corresponds to an expected shape of a non-flat surface of the solid sample, wherein the outer conductor and shaped conductor are arranged such that the outer and shaped conductors are centered about the longitudinal axis and are in electrical contact with each other; and
    wherein the shaped conductor and outer conductor are dimensioned such that the shaped conductor slides along an outer surface of the outer conductor while maintaining electrical contact with the outer conductor.

2. A sensor probe according to claim 1, wherein one or more spring members are positioned to apply a spring force between the outer conductor and the shaped conductor in directions parallel to the longitudinal axis.

3. A sensor probe according to claim 1, wherein the edge shape of the shaped conductor corresponds to a surface of the sample material having a shape selected from a group consisting of cylindrically convex, cylindrically concave, spherically convex and spherically concave.

4. A sensor probe according to claim 1, wherein the shaped conductor is removable from the sensor probe and is replaceable with a second shaped conductor that has an edge shape corresponding to a second expected shape of a non-flat surface of a solid sample.

5. A sensor probe according to claim 1, wherein the solid material is a core sample of rock from a subterranean rock formation.

6. A sensor probe system comprising:
    a sensor probe according to claim 1; and
    electronics configured to apply high frequency radiation into a solid sample from the central and shaped conductors.

7. A sensor probe system according to claim 6, wherein the electronics is further configured to measure a scattering parameter based at least in part on an interface between the sensor probe and the sample material.

8. A sensor probe system according to claim 7, wherein the electronics is further configured to derive one or more values for dielectric permittivity based at least in part on the scattering parameter measurements.

9. A sensor probe system according to claim 6, further comprising a stepper motor system positioned and configured to move the sensor probe into contact with the solid material at a plurality of locations on the solid material.

10. A sensor probe system according to claim 7, wherein the electronics is further configured to derive an anisotropy parameter of the solid sample based at least in part on measurements using the sensor probe.

11. A sensor probe system according to claim 10, further comprising a sample rotation system configured to rotate a cylindrical solid sample such that the sensor probe can take measurements of the solid sample at different orientations so as to facilitate derivation of the anisotropy parameter.

12. A sensor probe system according to claim 10, further comprising a second sample probe mounted to contact the solid sample at a direction that is rotated from that of the sample probe, the derivation of the anisotropy parameter being based on measurements from both the sample probe and the second sample probe.

13. A method of making dielectric measurements from a non-flat surface of a solid material using a coaxial sensor probe, the method comprising:
    moving a central conductor and a shaped conductor of a coaxial-based sensor probe into contact with the non-flat surface of the solid material, the shaped conductor having a circular cross section in a plane perpendicular to a longitudinal axis of the central conductor along at least a portion of the shaped conductor, and the shaped conductor having an edge shape that corresponds to the non-flat surface of the solid sample;

measuring a scattering parameter from an interface between the sensor probe and the sample material;

deriving one or more values for dielectric permittivity based at least in part on the scattering parameter measurements; and wherein the shaped conductor and outer conductor are dimensioned such that the shaped conductor slides along an outer surface of the outer conductor while maintaining electrical contact with the outer conductor.

14. A method according to claim 13, wherein the non-flat surface of the solid material is cylindrically or spherical shaped.

15. A method according to claim 13, wherein a motor system is used to move the coaxial-based sensor probe into contact with the solid material.

16. A method according to claim 15, further comprising:
making a first measurement with the sensor probe in contact with the solid material at a first location;
retracting the sensor probe away from the first location;
moving the sensor probe relative to the solid material and moving the sensor probe into contact with the solid material at a second location; and
making a second measurement with the sensor probe in contact with the solid material at the second location.

17. A method according to claim 15, further comprising:
moving the sensor probe relative to the solid material while maintaining contact with the solid material; and
making a series of measurements with the sensor probe as it is moved relative to the solid material.

18. A method according to claim 15, further comprising pushing the central conductor through the non-flat surface of the sample material so as to create an indentation on the non-flat surface.

19. A method according to claim 18, further comprising deriving one or more mechanical properties of the sample material based at least in part on the pushing of the central conductor through the non-flat surface of the sample material.

20. A method according to claim 19, wherein the one or more mechanical properties of the sample material includes uniaxial compressive stress (UCS).

21. A method according to claim 13, further comprising deriving an anisotropy parameter of the solid sample based at least in part on measurements using the sensor probe.

22. A method according to claim 21, wherein the anisotropy parameter is of a type selected from a group consisting of: permittivity and conductivity.

23. A method according to claim 13, further comprising:
removing the shaped conductor from the coaxial sensor probe; and
attaching a second shaped conductor to the coaxial sensor probe, the second shaped conductor having an edge shape corresponding to a second shape of a non-flat surface of a solid sample.

24. A method according to claim 13, wherein the solid sample is a core sample of rock from a subterranean rock formation.

25. A coaxial-based sensor probe for making dielectric measurements of a solid sample, the probe comprising:
a central conductor having a tip for contacting a surface of the solid sample, the central conductor defining a longitudinal axis of the probe;
a dielectric material surrounding at least a portion of the central conductor; and
an outer conductor surrounding at least a portion of the dielectric material, and having a circular cross section in a plane perpendicular to the longitudinal axis along at least a portion of the outer conductor, the outer conductor including an edge shape and position relative to the central conductor tip that corresponds to an expected shape of a non-flat surface of the solid sample such that electrical contact between the central conductor tip and the non-flat surface and electrical contact between the outer conductor and the non-flat surface are suitable for dielectric measurements of the solid sample.

26. A sensor probe according to claim 25, wherein the outer conductor edge has a shape corresponding to a convex and cylindrical shaped non-flat surface.

27. A sensor probe according to claim 25, wherein the outer conductor edge has a shape corresponding to a concave and cylindrical shaped non-flat surface.

28. A sensor probe according to claim 25, wherein the outer conductor edge extends beyond the central conductor tip which corresponds to a convex and spherical non-flat surface.

29. A sensor probe according to claim 25, wherein the central conductor tip extends beyond the outer conductor edge which corresponds to a concave and spherical non-flat surface.

* * * * *